(12) United States Patent
Ishikawa et al.

(10) Patent No.: US 7,275,453 B2
(45) Date of Patent: Oct. 2, 2007

(54) ANALYZING APPARATUS AND FINE PARTICLE COLLECTING APPARATUS

(75) Inventors: Masanori Ishikawa, Kokubunji (JP); Naoya Sasaki, Tomobe (JP); Katsumi Nagumo, Tokyo (JP); Shigenori Morishima, Fujisawa (JP); Hiroshi Naka, Komoro (JP)

(73) Assignee: Hitachi, Ltd., Tokyo (JP)

( * ) Notice: Subject to any disclaimer, the term of this patent is extended or adjusted under 35 U.S.C. 154(b) by 674 days.

(21) Appl. No.: 10/773,743

(22) Filed: Feb. 6, 2004

(65) Prior Publication Data

US 2005/0058575 A1    Mar. 17, 2005

(51) Int. Cl.
*G01N 1/00* (2006.01)
(52) U.S. Cl. .................. 73/864.33; 73/864
(58) Field of Classification Search ........... 73/864.33, 73/864, 863, 23.2
See application file for complete search history.

(56) References Cited

U.S. PATENT DOCUMENTS

| | | | |
|---|---|---|---|
| 3,908,969 A * | 9/1975 | Baum et al. ............... 266/89 |
| 3,998,626 A * | 12/1976 | Baum et al. ............... 75/385 |
| 5,425,263 A | 6/1995 | Davies et al. | |
| 5,465,607 A | 11/1995 | Corrigan et al. | |
| 5,854,431 A | 12/1998 | Linker et al. | |
| 5,964,985 A * | 10/1999 | Wootten ................ 201/40 |
| 6,013,158 A * | 1/2000 | Wootten ................ 202/99 |
| 6,334,365 B1 | 1/2002 | Linker et al. | |
| 6,408,701 B1 | 6/2002 | Fujita | |

FOREIGN PATENT DOCUMENTS

| | | |
|---|---|---|
| EP | 0447158 A2 | 9/1991 |
| EP | 0896213 A2 | 2/1999 |
| GB | 2376873 A | 12/2002 |
| JP | 2002-005811 | 1/2002 |
| WO | WO98/43063 A1 | 10/1998 |

* cited by examiner

*Primary Examiner*—Hezron Williams
*Assistant Examiner*—Rodney Frank
(74) *Attorney, Agent, or Firm*—Townsend and Townsend and Crew LLP (57) ABSTRACT

A simple and convenient analyzing apparatus is provided which easily, conveniently, and efficiently collects a material in the state of fine particles adhered to a target object, extracts the object to be analyzed, and analyzes the extracted object. An apparatus for detecting fine particles in a gas which sucks the gas under measurement from the target object by using a suction pump, extracts the fine particles contained in the gas under measurement, and performs measurement by using a spectrometer is embodied such that an inertial impactor for collecting the fine particles having diameters not less than a specified particle diameter is disposed upstream of the spectrometer, the fine particles are collected in the fine particle collector of the inertial impactor, the collector containing the collected fine particles is heated such that the collected fine particles are vaporized into a gas, and the vaporized fluid to be examined is supplied to the spectrometer to be measured thereby.

7 Claims, 11 Drawing Sheets

STATIONARY TYPE

MASS SPECTROMETER 3

INERTIAL IMPACTOR 1

4 SAMPLING PROBE

FIG. 9B

PORTABLE TYPE

INERTIAL IMPACTOR 1

MASS SPECTROMETER 3

4 SAMPLING PROBE

ANALYZING APPARATUS AND FINE PARTICLE COLLECTING APPARATUS

FIELD OF THE INVENTION

The present invention relates to an analyzing apparatus for analyzing the component of a fine particle material.

BACKGROUND OF THE INVENTION

It has been required to perform mass spectrometric analysis of a fine particle material contained in an atmosphere or another gas in terms of engineering, environmental problems, and the like.

For example, Japanese Patent Laid-Open No. 2002-5811 discloses removing unwanted fine particles of water vapor and the like in a gas therefrom and analyzing the remaining gas as an object to be examined. U.S. Pat. No. 6,334,365 discloses a detecting system for a human body, which is embodied to have a portal configuration through which a person passes and spray an air onto a person standing straight inside the port. U.S. Pat. No. 5,854,431 discloses a structure for collecting fine particles, which is embodied to apply a gas stream containing sample fine particles perpendicularly to a disposed filter and collect the sample fine particles.

[Patent Document 1] Japanese Patent Laid-Open No. 2002-5811

[Patent Document 2] U.S. Pat. No. 6,334,365

[Patent Document 3] U.S. Pat. No. 5,854,431

However, none of the foregoing embodiments is sufficient to perform easy, convenient, and efficient examination.

Examination is generally difficult in most cases for such reasons that: fine particles are normally an aggregate of molecules and it is impossible to specify the original molecules even though the fine particles can be measured as they are; the concentration of fine particles is low; and it is difficult to remove fine particles when they are adhered due to the strong adhesive force thereof. As part of anti-terrorism measures especially at an airport or the like, it has been increasingly necessary in recent years to detect dangerous materials. It is conceived that, among the dangerous materials, commonly used explosives such as TNT powder and RDX are normally in the state of fine particles because they are low in saturated vapor pressure and less likely to be vaporized. To specify and detect such a fine particle material, it is necessary to gasify the material with the application of heat by any means, introduce the resultant gas into a mass spectrometer, and perform measurement.

Conventionally, the measurement of such fine particles has been performed in such a manner that a person wipes off adhered fine particles by using a wipe-off sheet using a material such as cotton or the like and gasifies the fine particles with the application of heat. Japanese Patent Laid-Open No. 2002-5811 only discloses collecting the unwanted fine particles in the gas and measuring the remaining gas flow. In accordance with U.S. Pat. No. 6,334,365, the dangerous material detecting system is formed inevitably in large scale as a portal for a human body. Since a fine-mesh filter is used as a fine-particle collecting filter to collect the fine particles in accordance with U.S. Pat. No. 5,854,431, dust in an air inevitably adheres to the filter unless it is used in a clean environment. As a result, the efficiency of fine particle collection of the filter may conceivably be influenced if operation is performed constantly over a long period of time. In addition, scaling down is difficult if the flow rate is high because of the large loss factor of the filter.

In the case where clogging occurs, it becomes necessary to replace the filter and halt the system so that operation efficiency is lowered. If baggage checks for a variety of carry-on luggage at an airport or the like are taken as an example, the checks will conceivably become more stringent in the future as various explosives have been checked more rigorously in recent years as part of anti-terrorism measures. As a result of more stringent checks, influences such as a longer checking time and a delayed flight operation are observed. The number of air passengers and an amount of airfreight circulation are expected to increase in the future on a world-wide scale so that it is necessary to sufficiently reduce a checking time and labor and operation involved in checking.

On the other hand, the wipe-off method involves the operation of wiping off fine particles by a person and the operation of placing the wiped-off material in a heat gasifying mechanism. As a result, the problem is encountered that higher efficiency operation or automated operation is difficult to be performed.

To solve at least one of the foregoing problems, the present invention provides an apparatus for analyzing a fluid containing fine particles. An object of the present-invention is to provide an analyzing apparatus which allows, e.g., easy, convenient, and efficient checking to be performed.

SUMMARY OF THE INVENTION

To solve the foregoing problems, the present invention can have the following embodiments.

Accordingly, there is provided an analyzing apparatus, a fine particle recovering apparatus, or a fine particle collecting apparatus which performs in-line collection, concentration, and gasification of fine particles to allow reductions in testing time and labor and which is less likely to present a problem such as clogging induced by dust or the like.

This effectively promotes the procedure of collecting, concentrating, and gasifying fine particles for performing efficient mass spectrometric analysis of a fine particle material.

(1) In one aspect, the present invention is provided as an analyzing apparatus comprising a recovery unit for recovering a gas containing fine particles, a collection unit for collecting the fine particles from the gas recovered by the recovery unit, and an analysis unit to which components of the fine particles collected by the collection unit and vaporized are introduced, wherein the recovery unit has a cover, a nozzle for spraying a fluid to a target region to be examined which has the fine particles adhered thereto and is located inside the cover, and a recovery flow path for recovering the fluid sprayed to the target region, which is connecting to the collection unit.

(2) In another aspect, the present invention can be provided as a fine particle collecting apparatus. The fine particle collecting apparatus comprises a recovery unit for recovering a gas containing fine particles and a connecting path having a connection unit to a collection unit for collecting the fine particles from the gas recovered by the recovery unit. The recovery unit has a cover, a nozzle for spraying a fluid to a target region having the fine particles adhered thereto and located inside the cover, and a recovery flow path for recovering the fluid sprayed to the target region. Specifically, e.g., the fluid is ejected from the nozzle in a direction in which the ejected fluid approaches the recovery flow path. If the fluid ejected from the nozzle is expanded in the direction of ejection, the expansion can be defined at the center portion thereof. If the intensity of the ejected fluid is different depending on a direction, the fluid can be defined in a direction in which intensive ejection is mainly performed. The fluid may be, e.g., a pressurized air or the like.

(3) Preferably, the fine particle collecting apparatus is capable of concentrating and gasifying the collected fine particles. For this procedure, the fine particle collecting apparatus preferably comprises a recovery unit for sucking the fine particles, a collection unit for collecting the fine particles, a vaporizer for vaporizing the collected fine particles, an extraction flow path having a connecting portion to an analysis unit for guiding the vaporized fine particles, and an additional exhaust flow path for exhausting the gas that has passed through the collection unit.

For example, the fine particle collecting apparatus comprises a recovery unit for recovering a gas containing fine particles, and a collection unit for collecting the fine particles from the gas recovered by the recovery unit, wherein the collection unit has an ejector for ejecting the recovered gas, a fine particle collector disposed in opposing relation to the ejector to cause a collision between the fine particles in the gas, an exhaust flow path in which the gas that has passed through the fine particle collector flows, a vaporizer for vaporizing the fine particles collected by the fine particle collector, and an extraction flow path in which the components of the vaporized fine particles flow.

The fine particle collector composes, e.g., the wall of the gas flow path. The fine particle collector is constructed to intercept the ejected gas. The gas ejected from the ejector has its flow bent by the fine particle collector. The ejector is formed to have a flow path width smaller than that of the portion of the flow path located upstream thereof. This allows the flow speed of the ejected gas to be increased to a level higher than in the upstream portion of the flow path. The fine particle collector can also be formed to have a flow path width smaller than the portion downstream thereof. This allows the formation of an efficient flow.

By forming the heater of the vaporizer attached to the fine particle collector such that it has a size smaller than the diameter of the fine particle collector, a deposit portion of the fine particles on the fine particle collector can be heated selectively and effectively. Alternatively, the fine particle collector can be heated with a large output by forming the heater such that it has a size equal to or larger than that of the fine particle collector.

Preferably, the collection unit has each of the vaporizer for the collected fine particles and the extraction flow path disposed on a surface of the fine particle collector opposite to a side surface thereof formed with the ejector.

It can be considered that the fine particle collecting apparatus has a first operation of operating the suction pump to exhaust the gas toward the exhaust flow path and collecting the fine particles in the fine particle collector and a second operation of lowering the suction pump after the collection to suppress the exhaust of the gas toward the exhaust flow path and increasing a temperature of the fine particle collector to a level higher than during the first operation to vaporize the fine particles.

For example, it is preferable to perform control such that, when the fine particles are collected, the exhaust path is opened and the heater is turned OFF and that, when the fine particles are caused to flow into an analysis path, the heater is turned ON and the exhaust path is closed to cause the vaporized gas to flow, to the analysis unit, from the path to the analysis unit.

More preferably, the fine particle collector is embodied to include a plurality of fine particle collectors. For example, the fine particle collecting apparatus has a carry-in mechanism for carrying in the fine particle collector having the collected fine particles from the collection unit, a vaporizer for vaporizing the fine particles of the fine particle collector that has been carried in, and an extraction flow path in which the components of the vaporized fine particles flow. More specifically, the fine particle collecting apparatus comprises a support member on which the plurality of fine particle collectors are disposed, wherein a first one of the plurality of fine particle collectors is disposed at a position closer to the vaporizer and a second one of the plurality of fine particle collectors is disposed at a position closer to the collection unit.

It is also possible to construct, e.g., a dangerous material detecting apparatus for detecting a dangerous material by sucking in a gas under measurement by using a suction pump and measuring fine particles contained in the gas under measurement by using a mass spectrometer. An inertial impactor for collecting the fine particles having diameters not less than a specified particle diameter is disposed upstream of a mass spectrometer and the fine particles to be measured are collected in the fine particle collector by using the inertial impactor. The concentration of the fine particles is increased by performing the collection for a given length of time so that a target object at a high concentration is obtained. If operation is performed for a long period of time, fine particles at a high concentration can be collected. For example, the fine particles collected and concentrated by the inertial impactor are collected in the fine particle collector. The fine particles are heat gasified by using a heating element disposed in the fine particle collector such that they are introduced successfully into the mass spectrometer and measurement using the mass spectrometer is performed.

The present invention allows an analyzing apparatus capable of performing easy, convenient, and efficient checking to be provided.

BRIEF DESCRIPTION OF THE DRAWINGS

FIG. 1 is a structural view of an analyzing apparatus according to a first embodiment of the present invention;

FIG. 2 is a cross-sectional view of a fine particle collector of FIG. 1;

FIG. 3A is a cross-sectional view of an inertial impactor portion of FIG. 1 and FIG. 3B is a cross-sectional view taken along the line A-A' of FIG. 3A;

FIG. 4A is a cross-sectional view of an inertial impactor portion as an alternative to the inertial impactor portion of FIG. 3A and FIG. 4B is a cross-sectional view taken along the line A-A' of FIG. 4A;

FIG. 5A is a cross-sectional view of an inertial impactor portion as an alternative to the inertial impactor portion of FIG. 3A and FIG. 5B is a cross-sectional view taken along the line A-A' of FIG. 5A;

FIG. 6A is a cross-sectional view of an inertial impactor portion as an alternative to the inertial impactor portion of FIG. 3A and FIG. 6B is a cross-sectional view taken along the line A-A' of FIG. 6A;

FIG. 7A is a cross-sectional view of an inertial impactor portion as an alternative to the inertial impactor portion of FIG. 3A and FIG. 7B is a cross-sectional view taken along the line A-A' of FIG. 7A;

FIG. 8A is a cross-sectional view of an inertial impactor portion as an alternative to the inertial impactor portion of FIG. 3A and FIG. 8B is a cross-sectional view taken along the line A-A' of FIG. 8A;

FIGS. 9A and 9B are a general schematic views showing examples of the type of the analyzing apparatus of FIG. 1;

DESCRIPTION OF THE PREFERRED EMBODIMENT

Referring to the accompanying drawings, the embodiments of the present invention will be described herein below. The present invention is not limited by any of the specification of the present application, the scope of the claims, and the scope disclosed in the drawings and changes and modifications based on well-known technologies and the like are not prevented.

Figure 1:
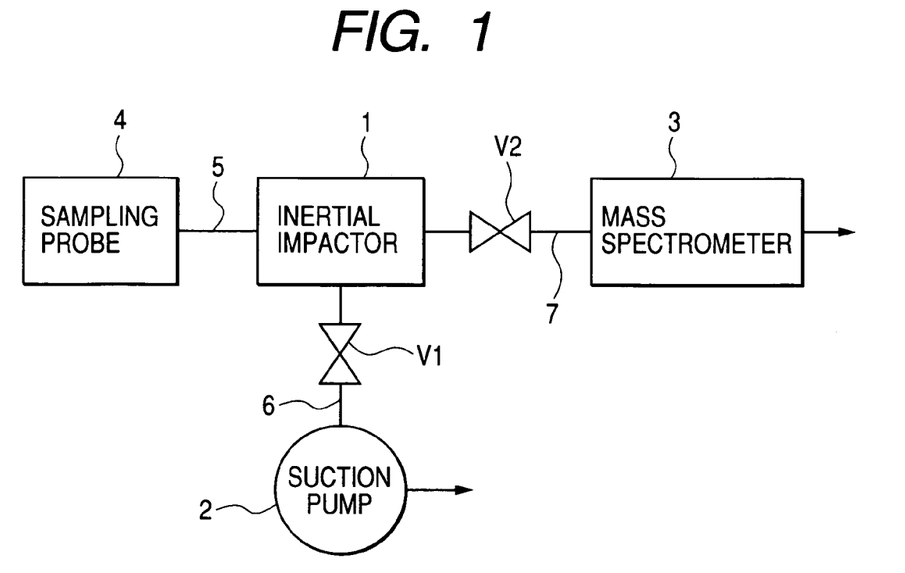
Figure 2:
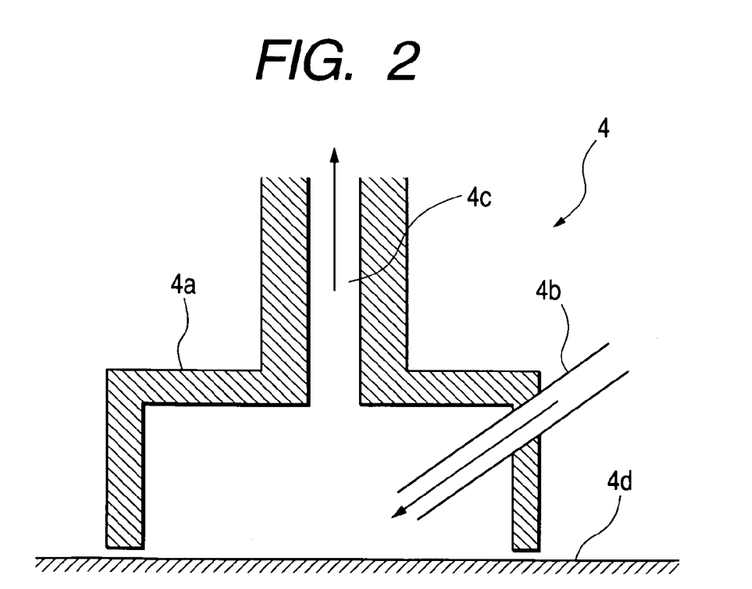
Figure 3A:
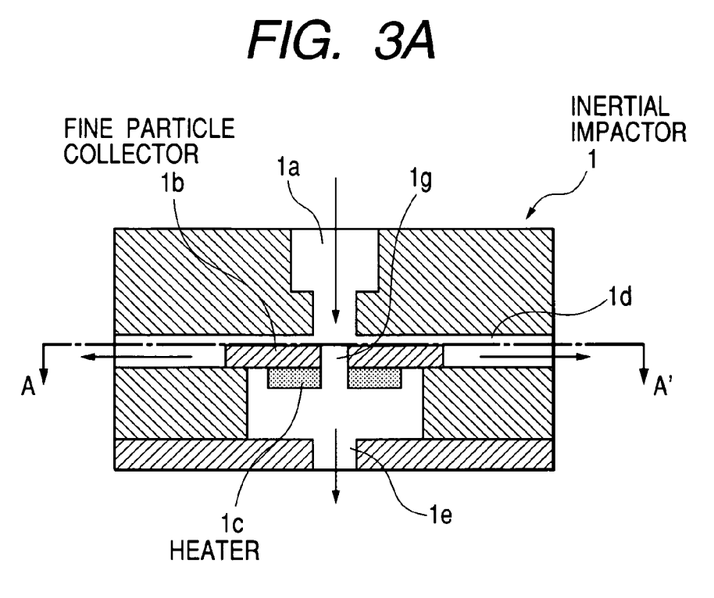
Figure 3B:
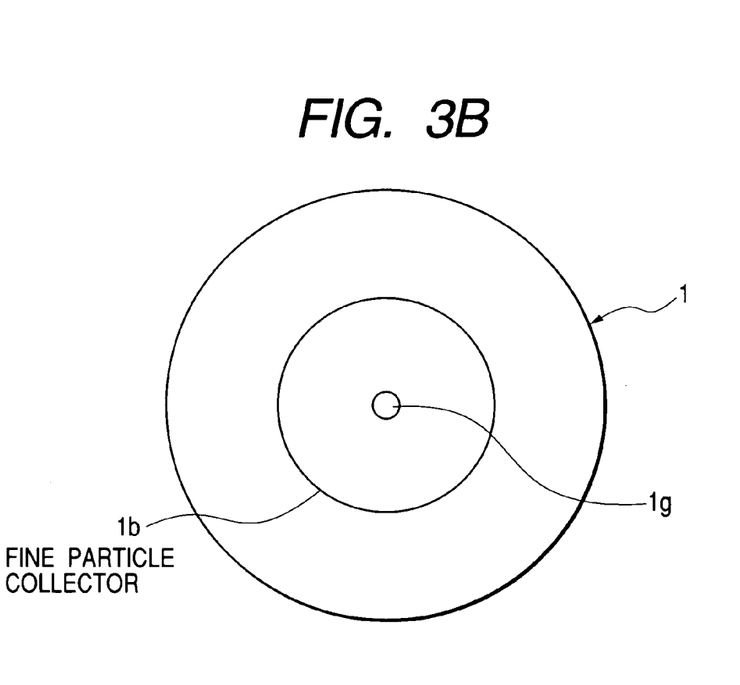
Figure 4A:
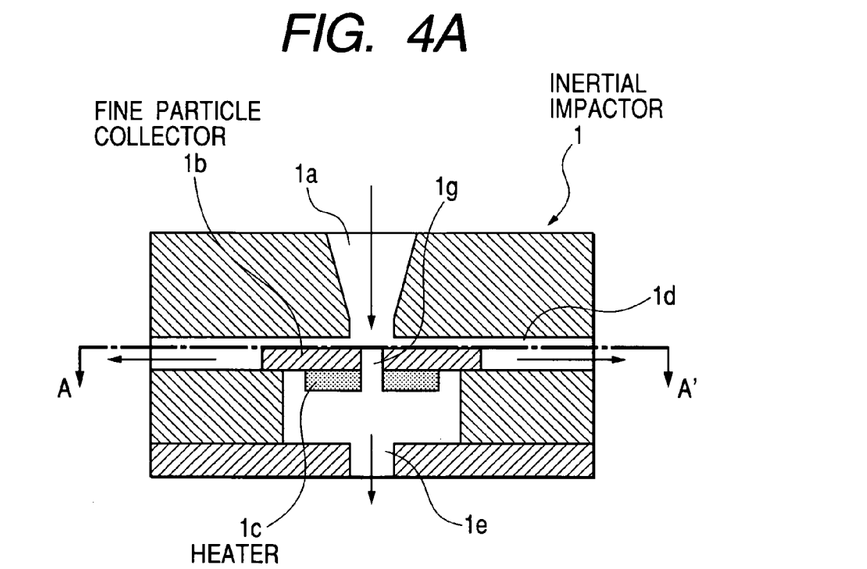
Figure 4B:
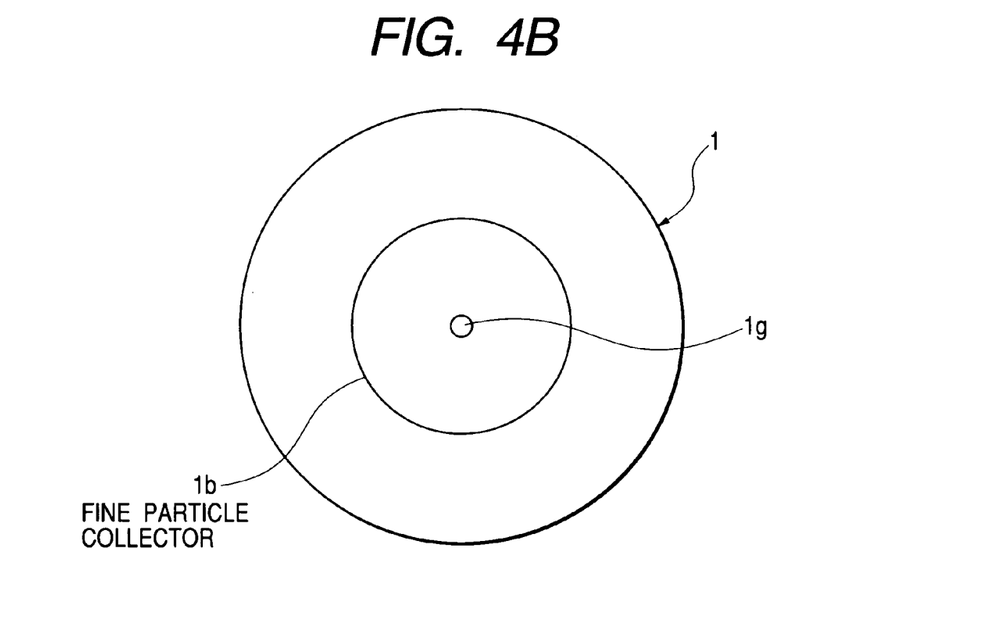
Figure 5A:
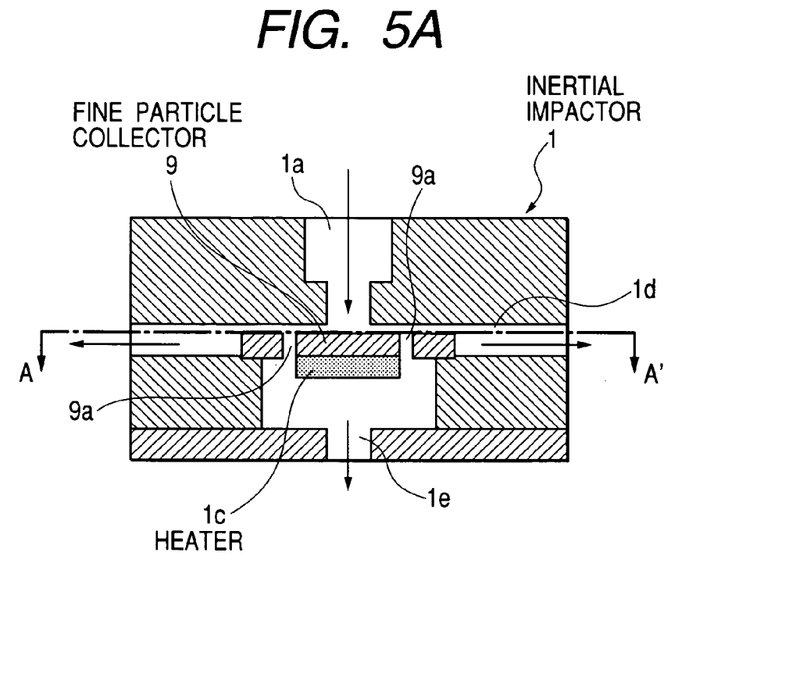
Figure 5B:
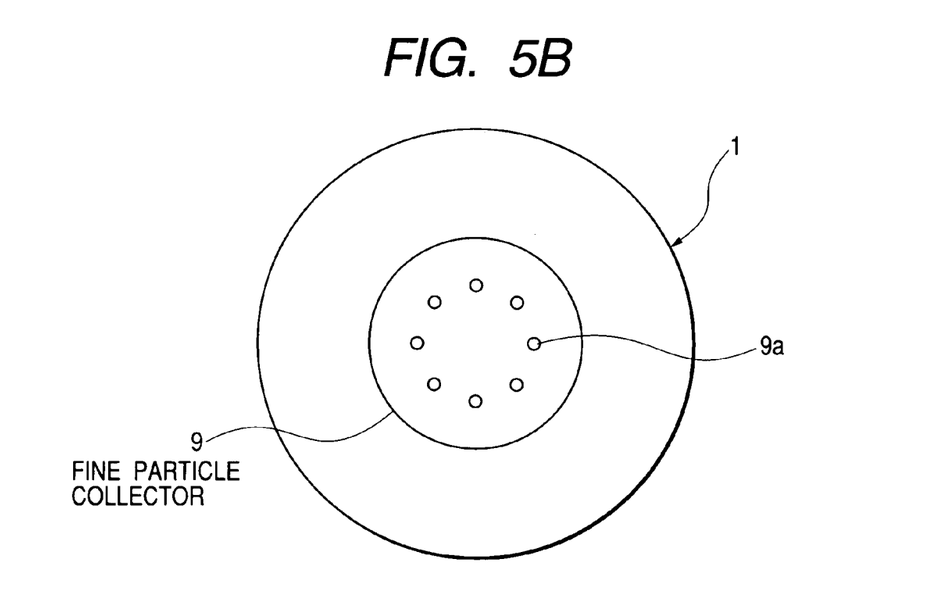
Figure 6A:
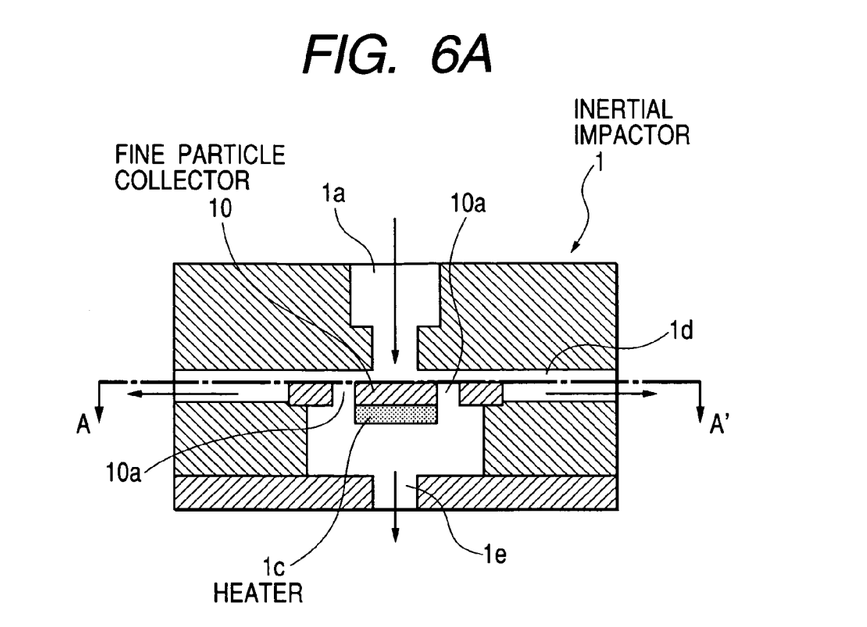
Figure 6B:
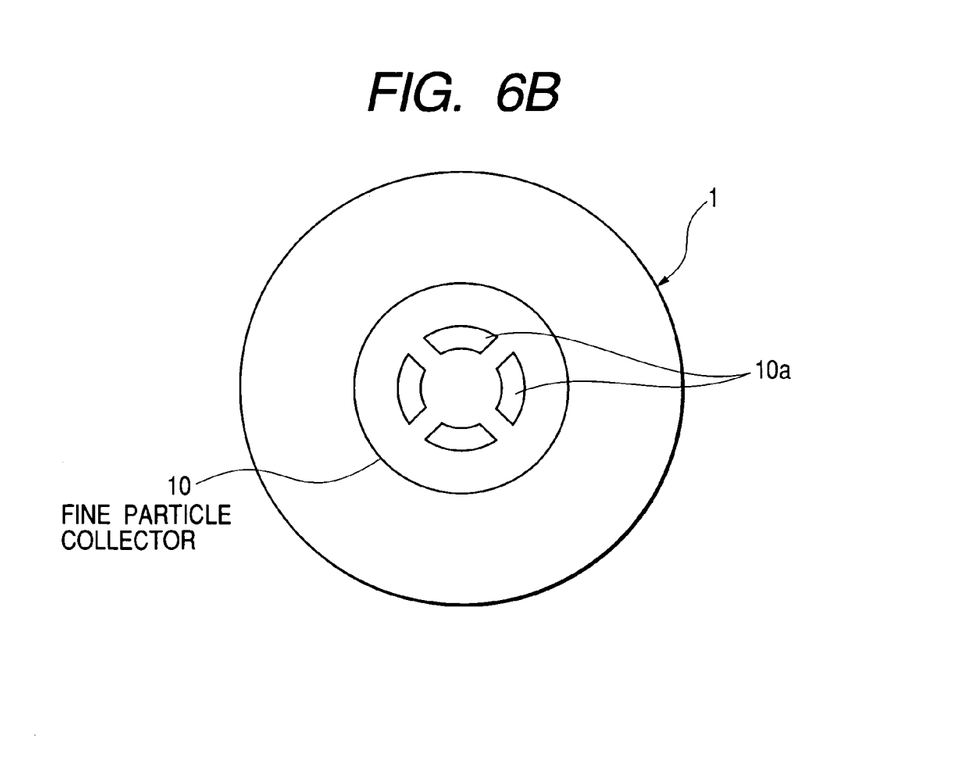
Figure 7A:
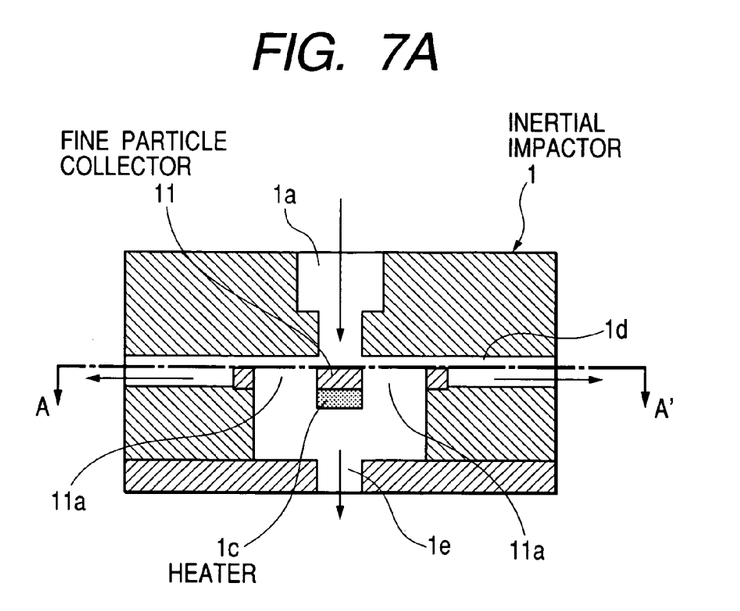
Figure 7B:
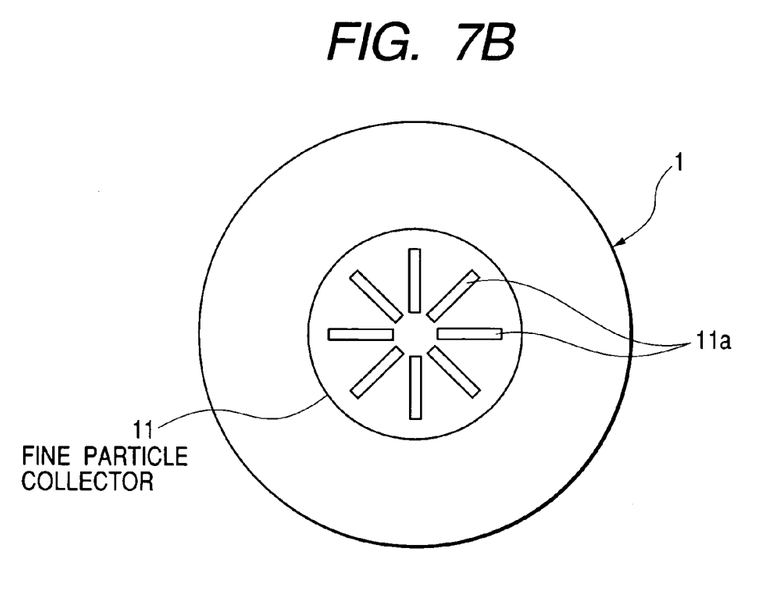

A first embodiment of the present invention will be described with reference to FIGS. 1 to 9. FIG. 1 is a structural view of an example of an analyzing apparatus including the mass spectrometer of a fine particle concentrating apparatus. FIG. 2 is a cross-sectional view of a sampling probe as a fine particle recovery unit. FIGS. 3A and 3B are cross-sectional views showing the collection of fine particles using the principle of an inertial impactor as a fine particle collector and a gasifier system.

Figure 9A:
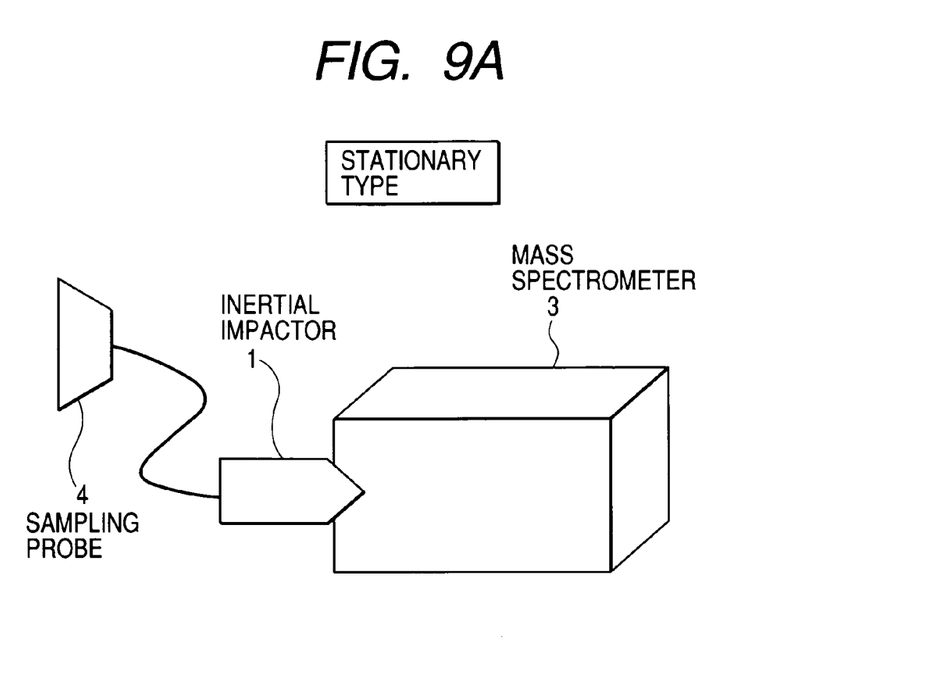
Figure 9B:
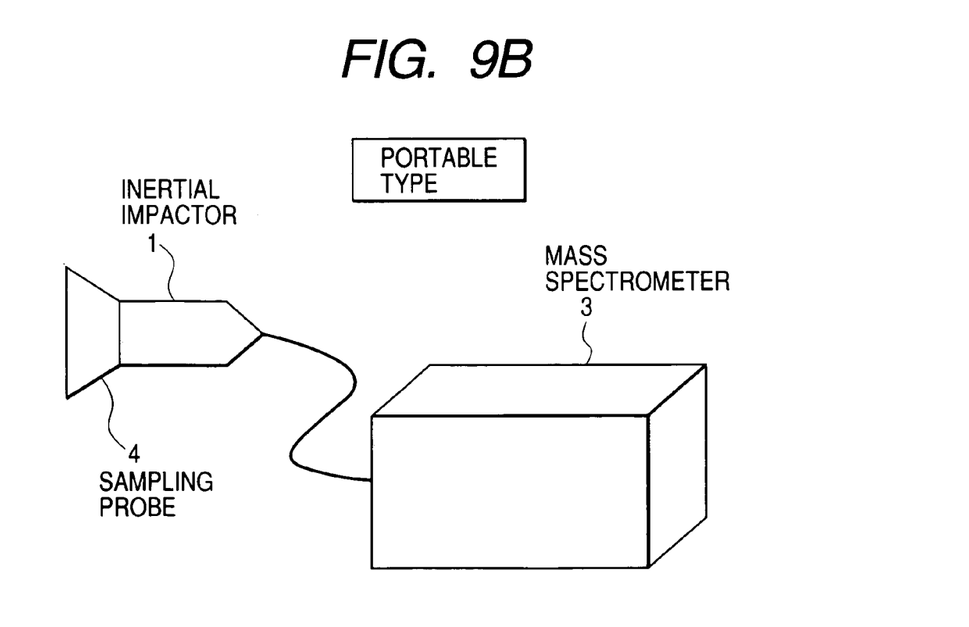

As shown in FIG. 9A, a stationary operation type can be considered in which a sampling probe 4 and an inertial impactor 1 are provided as separated structures and the inertial impactor 1 is attached to a mass spectrometric analyzing system 3 or fixed to a stage to be operated. Alternatively, a portable type can also be considered in which the inertial impactor 1 is formed integrally with the fine particle recovery unit or disposed in a close proximity to the fine particle collector, as shown in FIG. 9B, such that it connects to an analyzing system via a flow path.

Although the embodiment thus illustrates the form having the recovery unit, the collection unit, and the analysis unit, the recovery unit and the collection unit may also be provided as independent systems. If the recovery unit is provided as the independent system, the collection unit connecting thereto preferably has the form disclosed in the present embodiment, but it is not limited thereto. Likewise, if the collection unit is provided as the independent system, the recovery unit connecting thereto preferably has the form disclosed in the present embodiment, but it is not limited thereto. It is also possible to provide a system having the recovery unit and the collection unit or a system having the collection unit and the analysis unit. In this case also, the same shall apply.

A description will be given next to a basic structure, in which the sampling probe 4 is present and connected to the inertial impactor 1 via a pipe 5 as shown in FIG. 1. Pipes 6 and 7 are also connected to the inertial impactor 1, of which the pipe 6 is connected to the suction pump 2 to exhaust a gas that has passed through the inertial impactor 1 and the pipe 7 is connected to the mass spectrometer 3 to guide a target component to be examined. The pipes 5, 6, and 7 are connected to a fine particle entrance path 1a in FIGS. 3A and 3B, to an exhaust path 1d in FIGS. 3A and 3B, and to an extraction flow path 1e in FIGS. 3A and 3B, respectively. A valve V1 is disposed in the pipe 6 to adjust an amount of suction by the suction pump 2. A valve V2 is connected to the pipe 7 to adjust the gas flowing toward the mass spectrometer 3. A description will be given herein below to an example of an application to a dangerous material detecting apparatus for TNT powder, RDX, or the like. A mass spectrometric analyzing apparatus equipped with the fine particle concentrating apparatus according to the present invention allows anti-terrorism measures and anti-drug measures for screening out explosives and drugs to be taken for a carry-on luggage check at an airport or the like. It can be considered that these materials are normally present in the state of fine particles and adhered to the surface of luggage such as a bag. The materials present in the state of fine particles have an average particle diameter ranging from about 10 μm to about 30 μm, though the particle diameters differ depending on the materials. The flow rate and the size of the inertial impactor are optimized to allow collection of the fine particles in the size range. A consideration will be given to the case where an explosive or the like is adhered in the state of fine particles to the surface of a target object to be measured, such as a bag. First, the fine particles of an explosive or the like adhered to the surface of a bag or the like are removed by spraying an air or like method to be released into an air. For the removal, e.g., a method which removes the fine particles by spraying a jet of air or the like can be considered.

FIG. 2 shows an example of the recovery unit which is the sampling probe using an air jet. The recovery unit has a cover 4a, a nozzle 4b for spraying a fluid (which is a compressed air herein) onto a target region with the fine particles adhered thereto which is located inside the cover 4a, and a recovery flow path 4c for recovering the fluid sprayed onto the target region. In the recovery unit, an air is ejected from the nozzle 4b in a direction in which the ejected air approaches the recovery flow path 4c. By spraying the air jet from the jet spray nozzle 4b to the target region 4d to be examined, the fine particles are removed from the surface and conveyed through the recovery flow path 4c to the inertial impactor 1. Besides the gas jet spray structure, there may also be considered a structure in which a brush structure and a rotating roller structure, such as those provided in a vacuum cleaner or the like, are provided so that the fine particles are removed from the surface by bringing them into contact with the surface and operating them. For the fine particles to be dissociated from an object to which they are adhered and sucked, the provision of a dissociating mechanism such as a roller, a brush, or the like as a replacement for the foregoing gas ejector may also be considered. However, a fluid is ejected preferably in such a case where measurement is performed successively by changing target objects to be measured in consideration of contamination with the fine particles collected from the objects measured previously.

In the fine particle collector, the gas that has passed through the entrance path extending from the recovery unit to be ejected in divided relation from the ejector flows in a direction different from the direction of ejection to connect to the exhaust path.

Then, the removed particles are introduced into the inertial impactor as the fine particle collector from the suck-in portion of the inertial impactor 1. The pipe 5 in FIG. 1 and the fine particle entrance path 1a in FIGS. 3A and 3B correspond thereto. The inertial impactor 1 has a property which allows the collection of fine particles having diameters not less than a specified particle diameter and which is determined by the particle diameter, the flow rate, and the nozzle diameter. The fine particles enter the inertial impactor 1 from the flow path 1a. The flow path has an end composing the ejector for ejecting the gas containing the recovered fine particles, a fine particle collector 1b disposed in opposing relation to the ejector to cause collisions between the fine particles in the gas, the exhaust flow path 1*d* in which the gas that has passed through the fine particle collector 1*b* flows, a heater 1*c* used as an embodiment of a vaporizer for vaporizing the fine particles collected by the fine particle collector 1*b*, and the extraction flow path 1*e* in which the components of the vaporized fine particles flow.

In the fine particle collector 1*b*, the flow path is narrower in the outlet than in the inlet of the entrance portion so that the gas under measurement containing the fine particles is accelerated and ejected at a higher flow speed. The inertial impactor 1 is constructed such that the gas subsequently flows to the suction pump via the flow path 1*d*. Although the flow path 1*a* is a circular hole becoming larger and smaller in diameter, if the flow path 1*a* is formed into a nozzle structure such as the nozzle 1*a* which gradually narrows with approach toward the ejector at the end portion as shown in FIGS. 4A and 4B, efficient suction can be performed by reducing the influence of a pressure loss. The reason for providing such a nozzle portion is that, when fine particles are collected, the nozzle 1*a* of the inertial impactor 1 generally requires a high flow speed in accordance with the following principle. In the case where the flow path 1*a* of the inertial impactor 1 does not have the nozzle portion, if a required flow speed is to be obtained, a raise in suck-in flow rate can be considered. If it is assumed that the flow path 1*a* portion of the inertial impactor 1 has the same diameter as the inner diameter of the pipe 5, e.g., the flow rate should be raised to provide a high flow speed. This indicates that, at this time, the flow speed in the pipe 5 is the same as that in the flow path 1*a* portion of the inertial impactor 1, i.e., that a pressure loss in the pipe 5 is increased disadvantageously. It can therefore be said that the flow path 1*a* portion of the inertial impactor 1 having a nozzle configuration suppresses an increase in pressure loss and effective in providing a required high flow speed.

A description will be given to the fine particle collector in accordance with the principle of the inertial impactor in a downstream portion of the flow path 1*a*. The flow paths 1*a* to 1*d* have a configuration in which they cross orthogonally at the fine particle collector. Consequently, particles having sizes not less than the specified size cannot turn in the direction of the flow path 1*d* to collide against the fine particle collector 1*b* so that the fine particles are collected in the fine particle collector 1*b*. As a result, the inertial impactor 1 also has the effect of a filter. Uncollected particles having sizes not more than the specified size have been caught in a flow toward the suction pump where they are collected by the suction pump.

A basic numerical expression for giving a particle diameter d80 corresponding to the 80% collection efficiency of the inertial impactor 1 is as follows:

$$d80(Cc)^{1/2}=\{(9\times\eta\times N\times Stk80)/(\rho p\times U)\}^{1/2}$$

where d80: Particle Diameter (cm) Corresponding to 80% Collection Efficiency of Inertial Impactor 1, Cc: Cunningham Slip Correction Factor, η: Viscosity Factor (dynDsec/cm$^2$) of Air, N: Diameter (cm) of Nozzle 1*a*, Stk80: Number of Stokes corresponding to 80% Collection Efficiency of Inertial Impactor 1, ρp: Density of Particles (g/cm$^3$), and U: Average Speed (cm/sec) of Gas under Measurement at Nozzle 1*a*. In the numerical expression, if it is assumed that d50=1.0 μm=1.0×10$^{-4}$ (cm), Cc=1.2 (1 atmospheric pressure at 20° C.), η=1.81×10$^{-4}$ (dynDsec/cm$^2$), Stk80=0.20 (Stk80=0.25 in the case of a virtual impactor), ρp=1.0 (g/cm$^3$), and a sampling flow rate Φ=20.0 (1/min) are satisfied, the average speed U (cm/sec) of the gas under measurement at the nozzle 1*a* is given by U=4Φ/ΠN2. Therefore, the diameter N of the nozzle 1*a* can be determined as follows:

$$N=[\{4\times Cc\times\rho p\times(d50)2\times\Phi\}/\{9\times\Pi\times\eta\times Stk50\}]1/3=0.25(\mathrm{cm})=2.5(\mathrm{mm}).$$

Accordingly, if the inertial impactor 1 having a nozzle diameter N of 0.25 (cm) is used when the sampling flow rate Φ is 20.0 (1/min), it follows that particles having diameters d in excess of 1.0 μm (1.0×10$^{-4}$ cm) collide against the collector 1*b* with the 80% collection efficiency and are collected therein.

If it is assumed that the gap thickness of the exhaust path of the fine particle collector is S, S/N=1.0 is necessary. In an actual situation, however, S/N=1.0 or S/N=0.5 smaller than S/N=1.0 is necessary. In a type termed a virtual impactor, S/N=0.1 is necessary. Under this condition, the gap thickness S of the exhaust path in the fine particle collector becomes 0.01 (cm) and a possibility exists that a region where the influence of a pressure loss in the fluid cannot be circumvented is reached depending on the conditions. Therefore, caution is needed in the case of operation.

Thus, the fine particles having diameters not less than the specified diameter are collected in the fine particle collector of the inertial impactor. By continuing the operation for a given period of time, a quantity of fine particles deposited on the fine particle collector can be increased. The flow rate involved in mass spectrometric analysis when concentration is not performed ranges from 0.1 (L/min) to 1.0 (L/min). In the present invention, if it is assumed that suction is performed at an exhaust pump flow rate of 10 (L/min) or more, the flow rate ratio therebetween is 30:1 or more. Compared with the case where the impactor is not used, the number of fine particles that can be collected and used as target objects to be measured is equal to that in the case where suction is performed at the 30-fold flow rate provided that the suction time is the same. This achieves an improvement in sensitivity directly proportional to the flow rate ratio.

Even when the suction time is reduced to one third, a 10-fold improvement in sensitivity is expected. Conversely, if the suction time is elongated to about 3 times, it is considered that the sensitivity can be improved by 100 or more times.

Subsequently, suction is halted by stopping the suction pump 2 or bringing the valve V1 into a closed state. At this time, the fine particles are deposited in the fine particle collector.

The region of the flow path located in the vicinity of the fine particle collector 1*b* is smaller in cross-sectional area than the flow path 1*d* located downstream thereof. This is because a large pressure loss occurs in the fluid if the cross-sectional area of the flow path 1*d* is the same as in the vicinity of the fine particle collector, while the gap thickness required by the fine particle collector remains the same, so that it becomes necessary to compensate for the loss resulting from a misoperation of the apparatus due to an insufficient pump output or from the scaling up of the pump.

Then, the fine particle collector 1*b* is heated by using the heater 1*c* attached to the fine particle collector, whereby the deposited fine particles are gasified. The heating requires a temperature at which the fine particles as target objects to be measured are evaporated. In the present embodiment, a sheath heater is used as the heater 1c.

In the case of gasifying the fine particles, it is preferable to cause a rapid temperature increase. This is because the concentration of the gas can be increased by gasifying the concentrated fine particles within a short period of time.

This obviates the necessity to extract the fine particles by such means of wiping the collector 1b and gasify the fine particles if the measurement of the collected fine particles is performed subsequently, increases the sensitivity with the higher concentration of the fine particles, saves labor, allows on-line operation, and achieves higher efficiency. To solve the problem, the heating type can perform gasification inside the system and thereby achieves increased sensitivity, saved labor, on-line operation, and higher efficiency.

The gas thus obtained is supplied from a fine hole 1f provided in the fine particle collector 1b to the mass spectrometric analyzing system through the flow path 1e as the extraction flow path.

The higher concentration of the gas is achieved by adjusting a gasification time shorter than a collection time. The temperature of the fine particle collector 1b is not higher than the evaporation temperature for the fine particles and is controlled to be not lower than the evaporation temperature for the fine particles at the time of vaporization. In this case, the fine particle collector 1b is forcibly cooled by using a gas stream generated by operating the suction pump 2 or cooled to a specified temperature by adjusting the output of the heater 1c. The fine particle collector 1b has a narrowed flow path so that the flow speed of the gas under measurement, which also serves as a cooling gas, is high so that the forcible cooling achieves a high effect. To efficiently perform cooling, it is effective to bring the high temperature portion of the sample collector 1b into contact only with the portion at a high flow speed. It is also effective to reduce the width of the flow path and the size of the sample collector 1b.

It is assumed that the present embodiment is used in a situation such as a normal space at an airport or the like and the use thereof in a clean environment, such as a clean room, is not assumed. Accordingly, an object to be sucked is a normal atmosphere and it can be considered that extremely fine filth such as dust is contained therein. In the case of using a filtering method, the necessity to collect the fine particles leads to the necessity for a fine-mesh filter so that the frequency with which clogging occurs is increased. As a result, it becomes necessary to replace the filter or check clogging. However, the present embodiment is formed to suppress the occurrence of clogging at the fine particle collector 1b and allow stable collection. If dust or the like is deposited on the fine particle collector 1b, cleaning can also be performed by raising the flow rate to raise the flow speed in the fine particle collector 1b and thereby removing the adhered dust. In the case of performing an overhaul operation also, cleaning can be performed easily by forming the fine particle collector 1b into a simple structure such as a flat plate structure.

A specific operation of the present embodiment will be described. At the stage of collecting fine particles, the valve V1 is brought into the open state, while the valve V2 is brought into a closed state. As for the valve V2, it may also be brought into an open state provided that it does not interrupt the operation. This is because, since the suction speed of the mass spectrometer 3 is low compared with the suction speed of the suction pump 2 for the inertial impactor, the influence on a flow formed by the suction pump 2 can be considered to be small. Then, the suction pump 2 is operated to change the direction of the flow path from the flow path 1a at the fine particle collector 1b and then form a flow to the flow path 1d. At this time, the inertial impactor 1 is formed by properly setting the circumferential size of the fine particle collector so that the fine particles sucked into the fine particle collector 1b are collected. To collect the fine particles, it is necessary for the fine particle collector 1b to have a temperature not higher than the evaporation temperature for the fine particles. If heating by the heater 1c is held constant at a sufficiently high given temperature, e.g., 150° C., the temperature of the fine particle collector 1b is held constant by adjusting and controlling the output of the heater 1c. This is because a cooling effect is exerted by the suction, as stated previously. If the fine particle collector 1b is to be cooled maximally, it is allowed to cool without performing heating using the heater 1c. If the evaporation temperature at this time is assumed to be 200° C., however, a state at a given temperature or higher is preferred to a sufficiently cooled state if consideration is given to the effect of performing heating to a temperature not lower than 200° C. in a short period of time. Accordingly, it is conceivably effective to determine temperatures at which the fine particles are adsorbed but are not evaporated for different materials and perform settings.

Figure 8A:
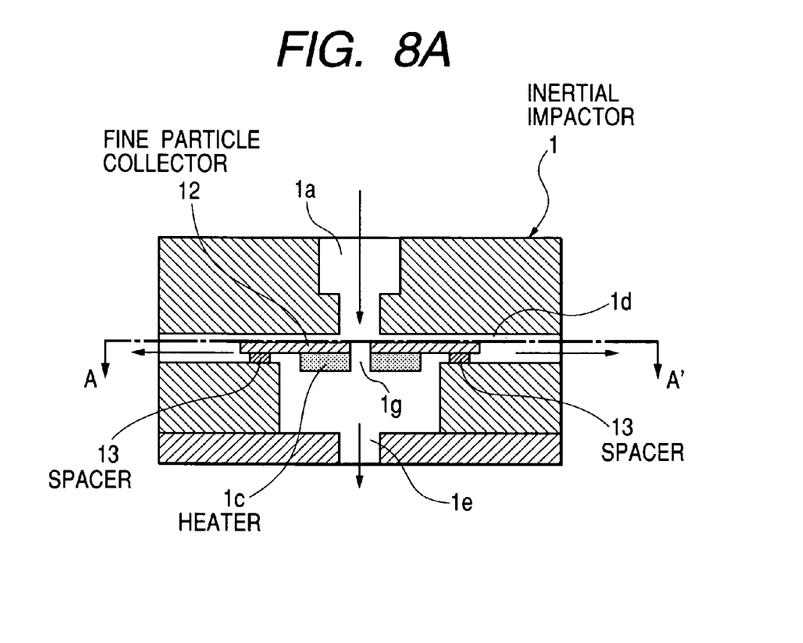
Figure 8B:
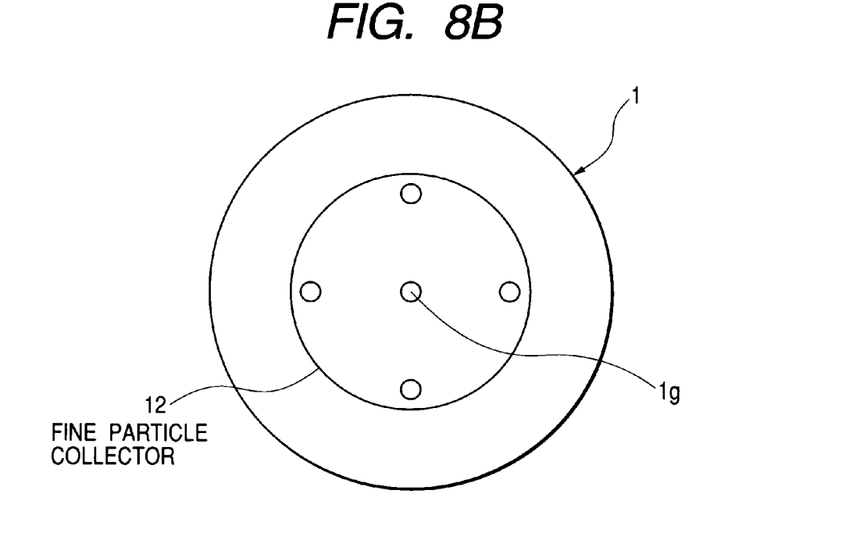

A description will be given to the configuration of a hole 1g in the fine particle collector 1b as the entrance path to the mass spectrometric analysis unit. If consideration is given to operation efficiency, it is necessary to perform the heating and cooling of the fine particle collector 1b in a short period of time. In the fine particle collector 1b in FIGS. 3A and 3B, the fine hole 1g is provided in the center portion of the fine particle collector 1b. The heat supplied from the heater 1c flows to the main body of the inertial impactor through the outer peripheral portion thereof, whereby the ultimate temperature and the heating efficiency are lowered. In the case where fine holes 9a or trenches 10a are formed by enclosing the center portion of the fine particle collector as shown in a fine particle collector 9 of FIGS. 5A and 5B and in a fine particle collector 10 of FIGS. 6A and 6B, the effect of narrowing a thermal path from the center portion to the outer peripheral portion and rendering the heat applied by the heater 1c less likely to be transferred to the outer peripheral portion is conceivably present. If the fine particles are adhered to the outer circumferences of the fine holes 9a or trenches 10a provided, there is a possibility that the removal of the fine particles by the suction of the vaporized gas and the application of heat becomes difficult. In the case where a plurality of trenches 11a are formed radially toward the outer peripheral portion as shown in a fine particle collector 11 of FIGS. 7A and 7B, the thermal path from the center portion is narrowed in the same manner as in the fine particle collector 9 of FIGS. 5A and 5B and in the fine particle collector 10 of FIGS. 6A and 6B and, in addition, the grooves 11a are formed also to the outer circumference. If there are fine particles collected at the outer peripheral portion, therefor, it may be considered that they are efficiently introduced into the mass spectrometric analyzing apparatus. However, it may also be considered that the flow to the exhaust path is interrupted conversely. As shown in FIGS. 8A and 8B, the connection area (heat transfer area) of the support member of the fine particle collector 12 is reduced by providing a spacer 13 in the connecting portion between a fine particle collector 12 and the inertial impactor 1. It can be considered to cut off the heat transfer path to the main body portion and thereby raise the heating efficiency. In the case of the present embodiment, the provision of four 0.2-mm spacers 13 each in the connecting portion to the main body made it possible to improve the heating efficiency. It was recognized that the heating time required to raise a room temperature to 200° C. was reduced to one third and the upper-limit temperature was also improved from 200° C. to 300° C. or more. This method can conceivably achieve higher effect when used in combination with the modification of the configuration of a hole in the fine particle collector. Although the present embodiment has primarily described the case where the heater 1c is smaller in size than the fine particle collector by way of example, if the heating of the main body side is performed simultaneously with the heating of the fine particle collector by using the heater 1c of the fine particle collector, it can be considered to make provisions by disposing the thermal path from the fine particle collector to the main body portion, by using the heater 1c equal in size to the fine particle collector, or by increasing the output of the heater. As another method, a reduction in the thickness or size of the fine particle collector 1b of the inertial impactor 1, the use of a material such as aluminum or copper instead of stainless steel, or the like is effective.

This allows a sequence of operations of removing, collecting, and gasifying the fine particles to be performed continuously. Even if the fine particles are at a low concentration, they can be detected by raising the concentration to a detectable level under the effect of concentration.

The embodiment described above allows an explosive in the state of fine particles to be collected and introduced into the mass spectrometric analyzer and also allows the sequence of operations of concentrating and gasifying the collected fine particles to be performed. Since this obviates the necessity for operation by a person, the operations can be increased in speed and efficiency. Since concentration is possible, fine particles at a low concentration which are normally difficult to detect can be detected. Furthermore, the simple structure promises improved maintainability and allows improved operation efficiency.

Figure 10:
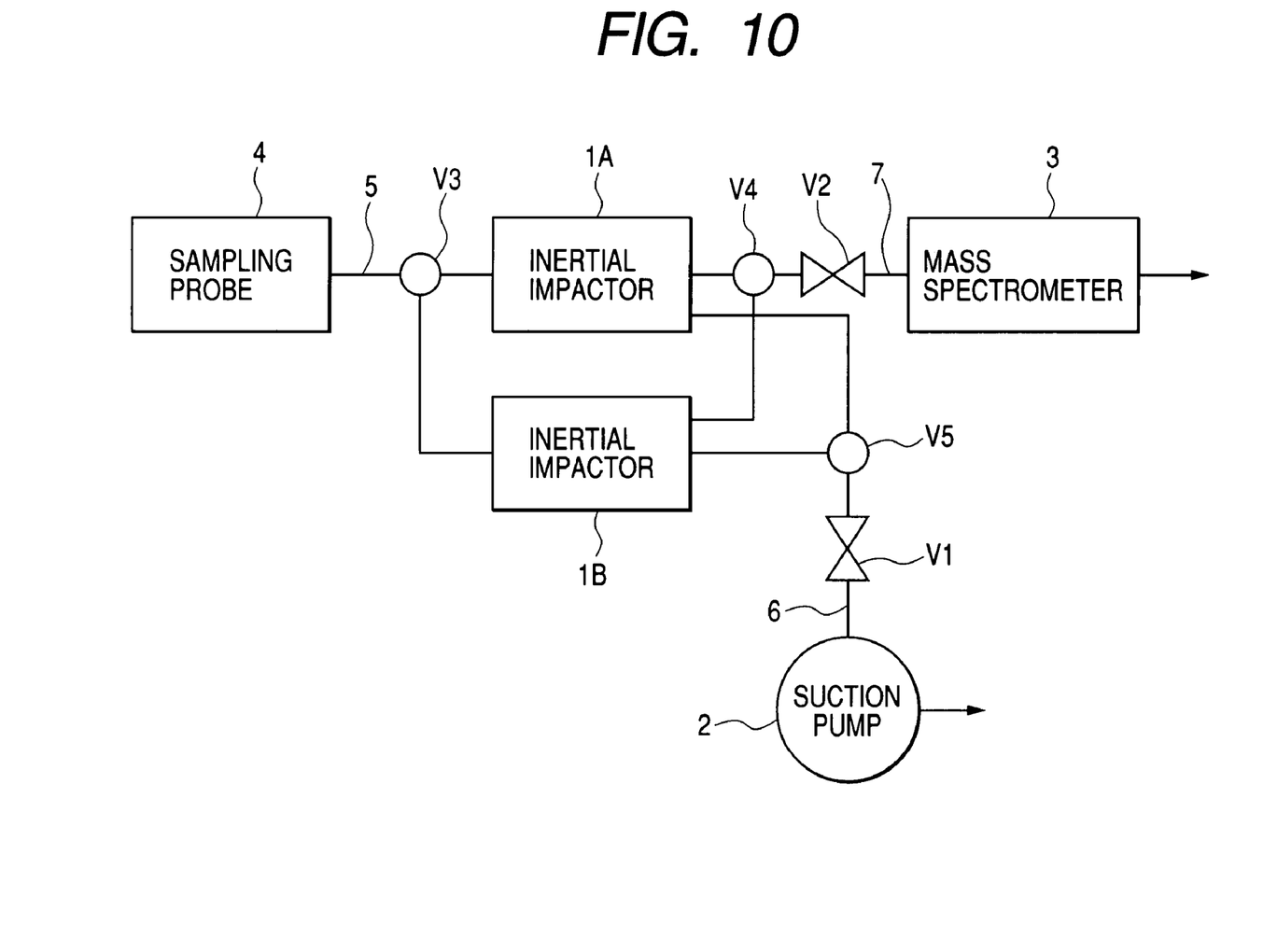
FIG. 10 is a structural view of an analyzing apparatus using a plurality of impactors according to a second embodiment of the present invention.

A second embodiment of the present invention will be described with reference to FIGS. 10 to 12. Basically, the second embodiment can use the structure of the foregoing embodiment and the form in which it is applied. The present embodiment is formed to have a plurality of fine particle collectors.

The arrangement improves the operation efficiency in a sequence of collecting, heat gasifying, and cooling processes by moving two or more inertial impactors 1 in parallel. An example which uses two inertial impactors and operates them in parallel is shown. In the example, the sampling probe 4 is used commonly, a switch valve V3 is disposed behind the sampling probe 4, and an air is introduced into an arbitrary one of the inertial impactors 1 disposed behind the switch valve V3. Behind the inertial impactors 1, a switch valve V4 is connected to the pipe 7 connecting to the mass spectrometer 3 and a switch valve V5 is connected to the pipe 6 connecting to the suction pump 2 so that opening and closing control is performed to prevent a backflow or the like in the inertial impactors. The order of opening and closing operations will be described later in detail in the description of the operation. FIG. 10 illustrates the case where two inertial impactors are used. The object of operating the inertial impactors in parallel is to continuously send a sample gas into the mass spectrometer 3. By dividing the operations into: collection/concentration and cooling; and heat gasification in two stages or into: collection/concentration; cooling; and heat gasification in three stages and successively switching the operations, the sample gas is supplied continuously. The two inertial impactors are termed A and B. It is assumed that collection is performed first by using the inertial impactor 1A. The suction pump 2 is operated to switch the switch valves V3 and V5 to the inertial impactor 1A. At the same time, the switch valve V4 is switched to the inertial impactor 1B to prevent the occurrence of suction. While the fine particles of an explosive are collected by using the inertial impactor 1A, the inertial impactor 1B operates the heater 1c such that heat gasification is performed and sends the sample gas to the mass spectrometer 3. Then, the valves V3 and V5 are switched to the position of the inertial impactor 1B. The switch valve V4 is switched to the inertial impactor 1A. While the inertial impactor 1B is performing cooling and collection, the inertial impactor 1A performs heat gasification to provide the sample gas.

Figure 11:
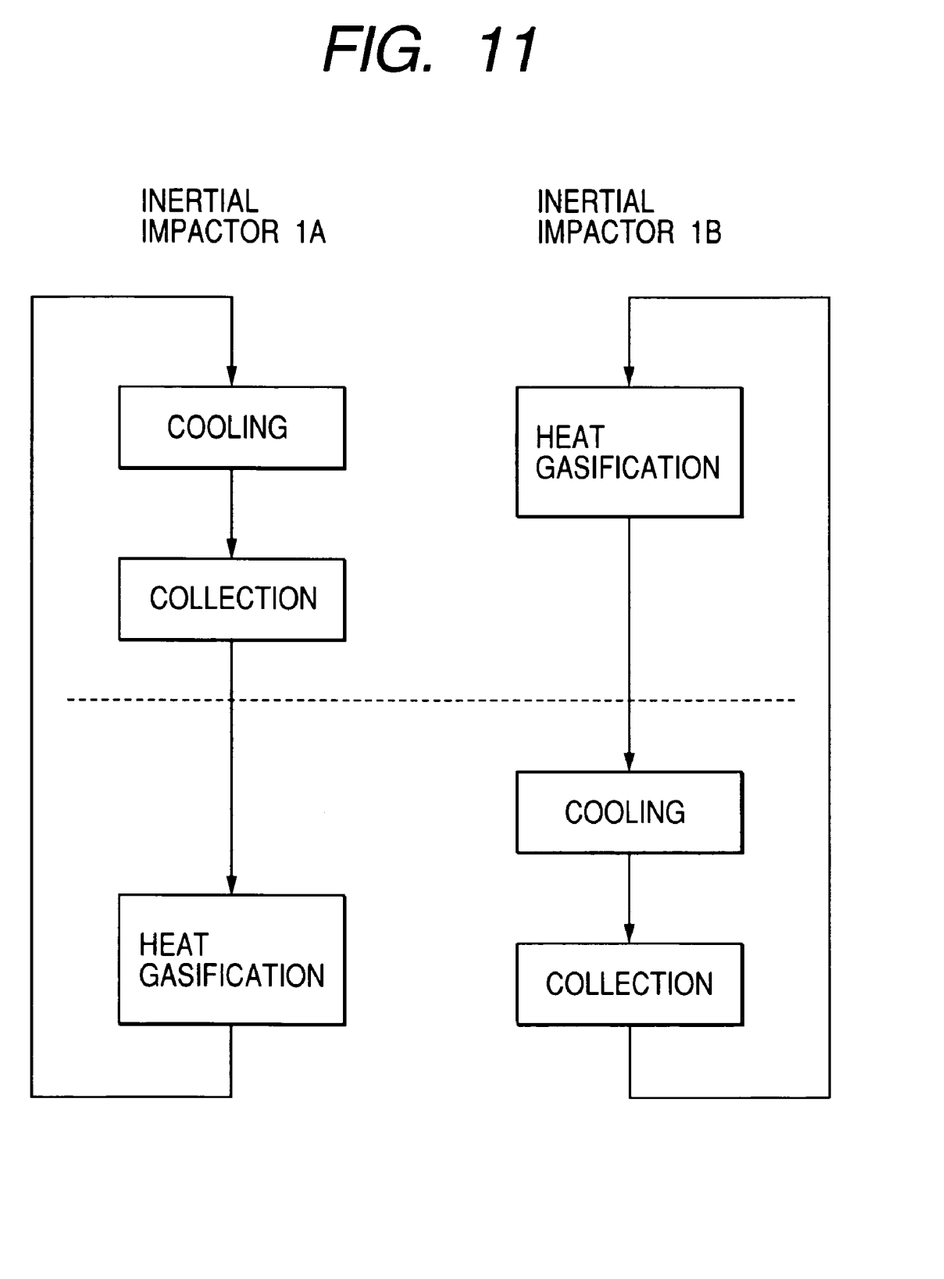
FIG. 11 is a process chart illustrating a case where the plurality of impactors of FIG. 10 are used.
Figure 12A:
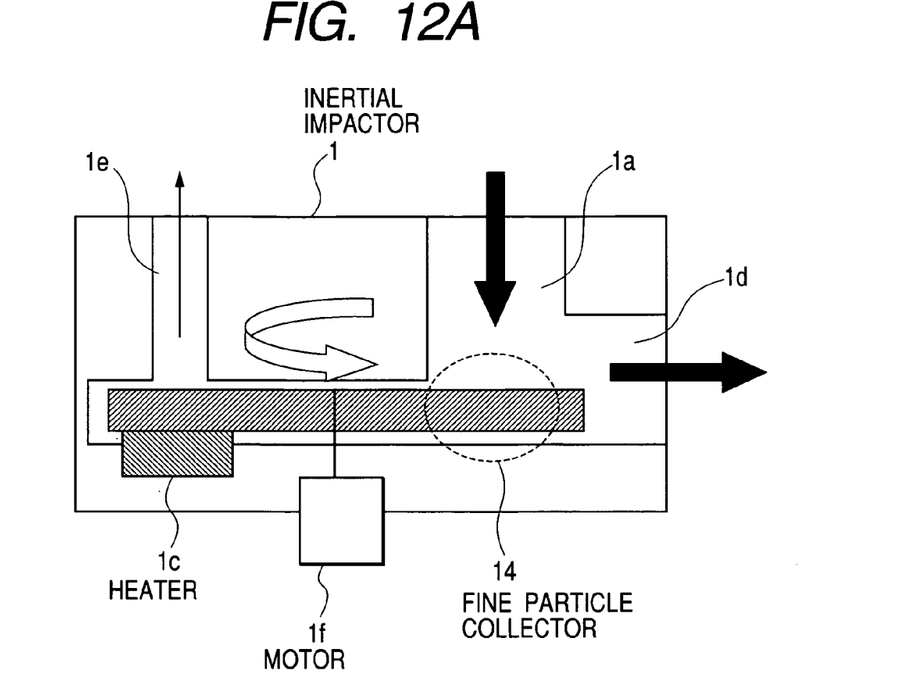
FIG. 12A is a cross-sectional view of a rotary impactor in the fine particle collector and FIG. 12B is a plan view of the impactor of FIG. 12A.
Figure 12B:
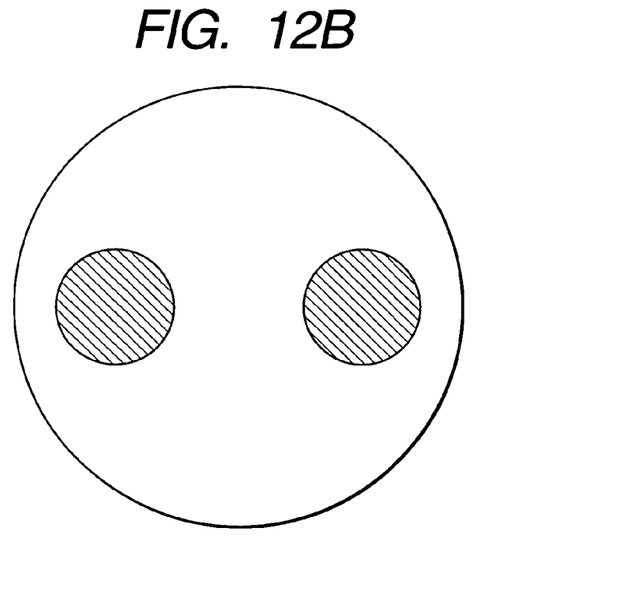

FIG. 11 shows a process chart. Since continuous collection can thus be performed, the time during which the supply of the sample gas stops is eliminated and the operation efficiency can be improved. In the case of using three or more inertial impactors, the intervals are adjusted by providing a long natural cooling time after heating. Specifically, natural cooling not involving the spraying of an air jet is performed first after heat gasification is completed and then forcible cooling using the air jet is performed. During the natural cooling, the collection and gasification of fine particles are performed by using another impactor.

A structure having a mechanism for moving the fine particle collector of the inertial impactor to perform collection/concentration, cooling, and heat gasification at different sites can be considered. FIGS. 12A and 12B show a structure using a rotating mechanism as the mechanism for moving the fine particle collector, in which the fine particle collector and a heat gasifier are provided discretely such that two separate processes are performed. After collecting the fine particles, the collected fine particles are moved to the heat gasifier by rotating a fine collecting plate by 180 degrees. At this time, cooling and collection of the fine particles are performed in the fine particle collector located on the opposite side of the fine particle collecting plate. This allows continuous gasification to be performed in the same manner as in the case where two inertial impactors are used.

Although the two collectors are provided in this example, if two or more collectors are provided, it can be considered to achieve higher efficiency by mounting an additional cooling mechanism separately from the collectors and independently providing the collectors, a heater, and a cooler.

Advantages offered by thus operating a collector/concentrator and a gasifier as one unit include an application to a portable type involving miniaturization, a cost reduction due to a simpler structure, a reduced amount of fine particles adhered to the wall surface due to a small area in contact with the heated sample gas, a noise reduction, and a reduction in operation time in each process, as stated previously.

What is claimed is:

1. An analyzing apparatus comprising:
a recovery unit for recovering a gas containing fine particles;
a collection unit for collecting said fine particles from the gas recovered by said recovery unit; and
an analysis unit to which components of said fine particles collected by said collection unit and vaporized are introduced, wherein
said collection unit has an ejector for ejecting the gas from said recovery unit, a fine particle collector disposed in opposing relation to said ejector to cause a collision between said fine particles in said gas, an exhaust flow path in which the gas that has passed through said fine particle collector flows, a vaporizer for vaporizing said fine particles collected by said fine particle collector, and an extraction flow path for guiding said vaporized components of said fine particle to said analysis unit.

2. The analyzing apparatus according to claim 1, wherein said collection unit has each of said vaporizer for the collected fine particles and said extraction flow path disposed on a surface of said fine particle collector opposite to a surface thereof formed with said ejector.

3. The analyzing apparatus according to claim 1, further comprising a carry-in mechanism for carrying in said fine particle collector having said collected fine particles from said collection unit and said vaporizer is formed to vaporize said fine particles of said fine particle collector that has been carried in.

4. An analyzing apparatus comprising:
a recovery unit for recovering a gas containing fine particles;
a collection unit for collecting said fine particles from the gas recovered by said recovery unit;
an exhaust flow path in which the gas that has passed through said collection unit flows and a suction pump is disposed; and
an analysis unit to which components of said fine particles collected by said collection unit and vaporized are introduced, wherein
said collection unit has an ejector for ejecting the gas from said recovery unit, a fine particle collector disposed in opposing relation to said ejector to cause a collision between said fine particles in said gas, a vaporizer for vaporizing said fine particles collected by said fine particle collector, and an extraction flow path for guiding said components of said vaporized fine particles to said analysis unit, said analyzing apparatus having
a first operation of operating said suction pump to exhaust the gas toward said exhaust flow path and collecting said fine particles in said fine particle collector and a second operation of lowering said suction pump after said collection to suppress the exhaust of the gas toward the exhaust flow path and increasing a temperature of said fine particle collector to a level higher than during said first operation to vaporize said fine particles.

5. A fine particle collecting apparatus comprising:
a recovery unit for recovering a gas containing fine particles; and
a collection unit for collecting said fine particles from the gas recovered by said recovery unit, wherein
said collection unit has an ejector for ejecting the gas from said recovery unit, a fine particle collector disposed in opposing relation to said ejector to cause a collision between said fine particles in said gas, an exhaust flow path in which the gas that has passed through said fine particle collector flows, a vaporizer for vaporizing said fine particles collected by said fine particle collector, and an extraction flow path in which said components of said vaporized fine particles flow.

6. A fine particle collecting apparatus comprising:
a recovery unit for recovering a gas containing fine particles; and
a collection unit for collecting said fine particles from the gas recovered by said recovery unit, wherein
said collection unit has an ejector for ejecting the gas that has passed through said recovery unit, a fine particle collector disposed in opposing relation to said ejector to cause a collision between said fine particles in said gas, an exhaust flow path in which the gas that has passed through said fine particle collector flows, a carry-in mechanism for carrying in said fine particle collector having said collected fine particles from said collection unit, a vaporizer for vaporizing said fine particles of said fine particle collector that has been carried in, and an extraction flow path in which said components of said vaporized fine particles flow.

7. A fine particle collecting apparatus comprising:
a recovery unit for recovering a gas containing fine particles; and
a collection unit for collecting said fine particles from the gas recovered by said recovery unit, wherein
said collection unit has an ejector for ejecting the gas that has passed through said recovery unit, a fine particle collector disposed in opposing relation to said ejector to cause a collision between said fine particles in said gas, an exhaust flow path in which the gas that has passed through said fine particle collector flows and which is connecting to a suction pump, a vaporizer for vaporizing said fine particles collected by said fine particle collector, and an extraction flow path in which said components of said vaporized fine particles flow, said fine particle collecting apparatus having
a first operation of operating said suction pump to exhaust the gas toward said exhaust flow path and collecting said fine particles in said fine particle collector and a second operation of lowering said suction pump after said collection to suppress the exhaust of the gas toward the exhaust flow path and increasing a temperature of said fine particle collector to a level higher than during said first operation to vaporize said fine particles.

* * * * *